(12) United States Patent
Lin

(10) Patent No.: US 8,964,022 B2
(45) Date of Patent: Feb. 24, 2015

(54) DYNAMIC IMAGING SYSTEM

(71) Applicant: Quanta Computer Inc., Guishan Dist., Taoyuan (TW)

(72) Inventor: Chin-Lin Lin, Kuei Shan Hsiang (TW)

(73) Assignee: Quanta Computer Inc., Guishan Dist., Taoyuan (TW)

( * ) Notice: Subject to any disclaimer, the term of this patent is extended or adjusted under 35 U.S.C. 154(b) by 314 days.

(21) Appl. No.: 13/675,562

(22) Filed: Nov. 13, 2012

(65) Prior Publication Data

US 2014/0078290 A1   Mar. 20, 2014

(30) Foreign Application Priority Data

Sep. 18, 2012   (TW) .............................. 101134091 A

(51) Int. Cl.
*H04N 7/18* (2006.01)
*B65G 43/08* (2006.01)
*G01N 21/88* (2006.01)

(52) U.S. Cl.
CPC ................ *H04N 7/188* (2013.01); *B65G 43/08* (2013.01); *G01N 21/8806* (2013.01)
USPC .............................................. 348/92; 348/86

(58) Field of Classification Search
CPC ......... H04N 7/188; H04N 7/18; H04N 7/183; B65G 43/08; G01N 21/8806; G01N 21/88; G06T 2207/30164; G06T 7/0004; G06T 7/001
USPC ............... 348/92, 86, 61, 125, 126, 129, 133, 348/134, 190; 382/141; 700/95, 108–110; 702/35
IPC .............................................. H04N 7/18, 17/00
See application file for complete search history.

(56) References Cited

U.S. PATENT DOCUMENTS

| | | | | |
|---|---|---|---|---|
| 6,046,764 | A * | 4/2000 | Kirby et al. ..................... | 348/92 |
| 7,145,595 | B2 * | 12/2006 | Yamane et al. ................. | 348/92 |
| 2010/0188500 | A1 * | 7/2010 | Bouchard et al. .............. | 348/93 |
| 2010/0309308 | A1 * | 12/2010 | Saphier et al. ................. | 348/92 |

* cited by examiner

*Primary Examiner* — Sherrie Hsia
(74) *Attorney, Agent, or Firm* — McClure, Qualey & Rodack, LLP

(57) ABSTRACT

A dynamic imaging system is provided. The system includes an assembly line, for an object to be placed thereon and for moving the object in a moving direction; a sensor set, for sensing a moving speed and the width of the object on the assembly line; a photography device, for capturing images of the object; and a controller, coupled to the sensor set and the photography device, for controlling the photography device to move and capture images of the object according to the moving speed and the width of the object.

12 Claims, 2 Drawing Sheets

DYNAMIC IMAGING SYSTEM

CROSS REFERENCE TO RELATED APPLICATIONS

This Non-provisional application claims priority under 35 U.S.C. §119(a) on Patent Application No(s). 101134091, filed in Taiwan, Republic of China on Sep. 18, 2012, the entire contents of which are hereby incorporated by reference.

BACKGROUND OF THE INVENTION

1. Field of the Invention

The present invention relates to dynamic imaging systems, and in particular, relates to dynamic imaging systems for inspecting products.

2. Description of the Related Art

In the prior art, imaging systems are frequently used to capture images of products on assembly lines. By comparing the captured images with a standard image, quality control inspections may be automatically implemented, decreasing manual labor costs. For example, the positioning and printing of keys or labels on a laptop computer can be inspected.

However, the assembly line is not static and is moving, and the speed at which it is moving may vary due to the weight and placement of products and various other factors. Thus, traditional image systems usually require high-grade cameras or must properly increase image capturing speed (i.e., shorten the shutter time) so as to obtain the required images.

BRIEF SUMMARY OF THE INVENTION

The present invention provides a dynamic imaging system. The system comprises an assembly line, for an object to be placed thereon and for moving the object in a moving direction; a sensor set, for sensing a moving speed and the width of the object on the assembly line; a photography device, for capturing images of the object; and a controller, coupled to the sensor set and the photography device, for controlling the photography device to move and capture images of the object according to the moving speed and the width of the object.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The present invention aims to improve conventional dynamic imaging system technology. In an embodiment, the dynamic imaging system of the present invention is implemented for product inspection purposes, However, the present invention should not be limited thereto.

Dynamic Imaging System

Figure 1:
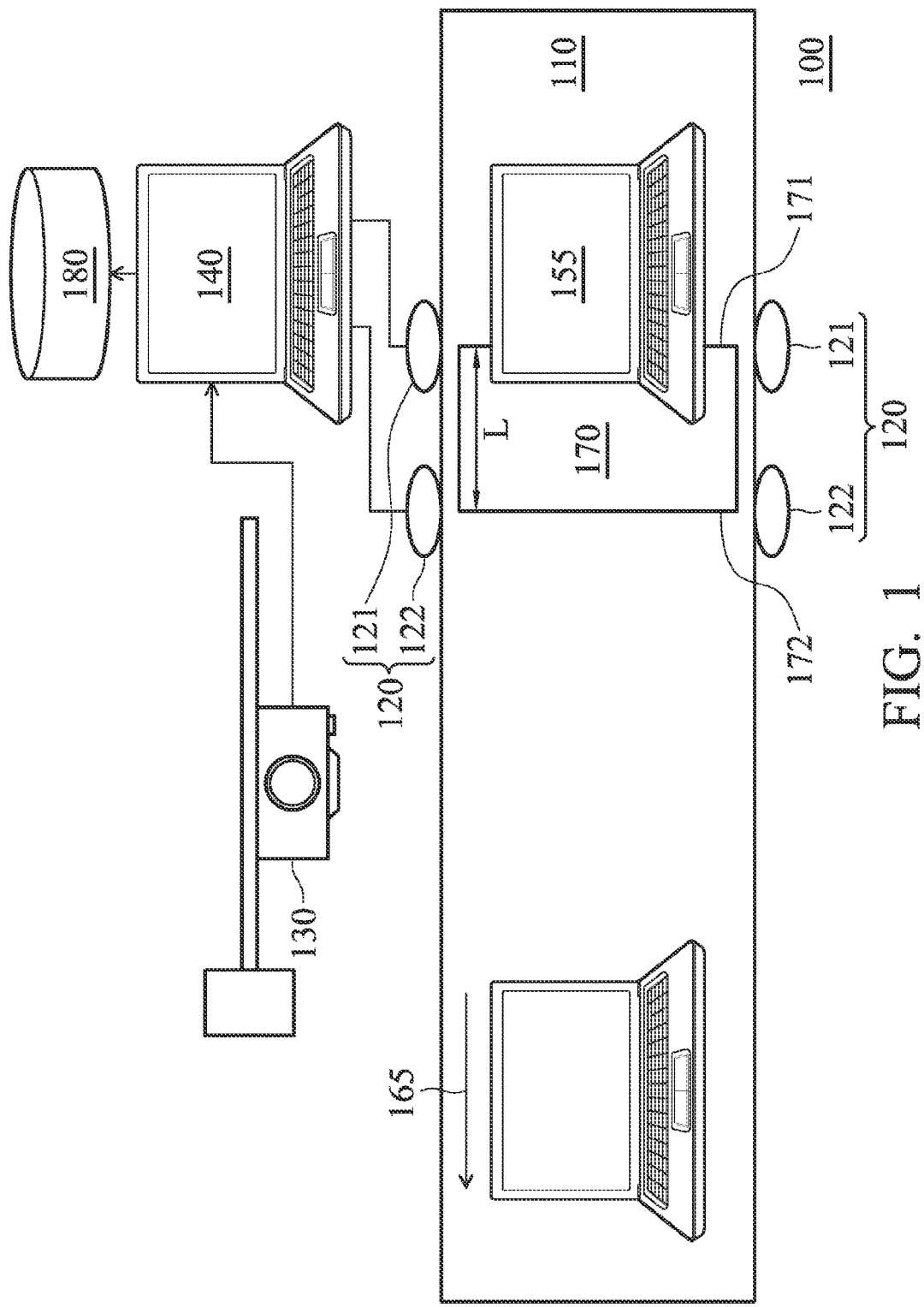
FIG. 1 is a schematic diagram of a dynamic imaging system according to an embodiment of the present invention.

FIG. 1 is a schematic diagram of a dynamic imaging system according to an embodiment of the present invention. The dynamic imaging system 100 at least comprises an assembly line 110, a sensor set 120, a photography device 130 and a controller 140. An object 155 can be placed on the assembly line 100, and the assembly line 100 can move the object 155 in a moving direction (as shown by arrow 165). The object can be any product which traditionally, requires human visual examination, such as a notebook computer keyboard, or a printed circuit board, etc.

The sensor set 120 of the present invention can be used to sense the moving speed V and the width W of the object 155 which is on the assembly line 110. In an embodiment, the sensor set 120 of the present invention further comprises a first sensor 121 and a second sensor 122, which are respectively disposed on a first terminal 171 and a second terminal 172 of a measuring region 170 for the assembly line 110. For example, the sensor 121 (or 122) can be an optical sensor having two parts which are respectively disposed on the opposite sides of the assembly line 110, as shown in FIG. 1. An object 155 is detected when one part of the sensor can not receive the light sent by the other part due to the obstruction of the object 155 on the assembly line 110. As shown in FIG. 1, the distance between the first terminal 171 and the second terminal 172 is defined as the length of the measuring region 170.

In an embodiment, when the leading edge of the object 155 passes the first terminal 171 of the measuring region 170, the first sensor 121 is triggered and records a first leading-edge-triggered time Tf1. The first leading-edge-triggered time Tf1 is the time that the leading edge of the object enters the measuring region 170. Then, when the leading edge of the object 155 passes the second terminal 172 of the measuring region 170, the second sensor 122 is triggered and records a second leading-edge-triggered time Tf2. The second leading-edge-triggered time Tf2 is the time that the leading edge of the object leaves the measuring region 170. In this embodiment, with the first leading-edge-triggered time Tf1, the second leading-edge-triggered time Tf2 and the length of the measuring region L, the controller 140 of the present invention can calculate the moving speed V of the assembly line 110, where V is equal to L/(Tf2−Tf1).

Similarly, in another embodiment, the moving speed V can be calculated based on the time that the trailing edge of the object 155 enters and leaves the measuring region 170. Specifically, when the trailing edge of the object 155 passes the first terminal 171 of the measuring region 170, the first sensor 121 is triggered and records a first trailing-edge-triggered time Tr1. The first trailing-edge-triggered time Tr1 is the time that the trailing edge of the object enters the measuring region 170. Then, when the trailing edge of the object 155 passes the second terminal 172 of the measuring region 170, the second sensor 122 is triggered and records the second trailing-edge-triggered time Tr2. The second trailing-edge-triggered time Tr2 is the time that the leading edge of the object 155 leaves the measuring region 170. In this embodiment, with the first trailing-edge-triggered time Tr1, the second trailing-edge-triggered time Tr2 and the length of the measuring region L, the controller 140 of the present invention can calculate the assembly line 110 moving speed V of the assembly line 110, where V is equal to L/(Tr2−Tr1).

In the previous embodiment, the present invention calculates the moving speed V by detecting the leading and trailing edges of the object 155; however, the present invention should not be limited thereto. In other embodiments, those skilled in the art can set the controller 140, according to the spirit of the present invention, so as to calculate the moving speed V by detecting the time that any specific position of the object 155 enters and leaves the measuring region 170.

The controller 140 can calculate the width W of the object 155 according to the time records previously obtained by the sensors 121 and 122. In an embodiment, the width W of the object 155 can be calculated based on the first leading-edge-triggered time Tf1, the first trailing-edge-triggered time Tf2 and the moving speed V of the object 155, where the width W is equal to (Tf2−Tf1)×V. Alternatively, in another embodiment, the width W of the object 155 can be calculated based on the second leading-edge-triggered time Tr1, the second trailing-edge-triggered time Tr2 and the moving speed V of the object 155, wherein the moving speed V is equal to (Tr2−Tr1)×V.

The photography device 130 of the present invention comprises an industrial camera for image capturing the object 155. In an embodiment, the industrial camera can be driven by a servo motor so as to move on a rail in parallel to the assembly line 110.

Finally, the controller 140 of the present invention can control the moving and image capturing of the photography device 130 according to the calculated moving speed V and width W, and obtain an image of the object 155 where the object 155 looks still. Specifically, in an embodiment before image capturing of the object 155, the controller 140 makes the photography device 130 accelerate from rest to the moving speed V, and then causes the photography device 130 to follow the object 155 with the moving speed V while capturing images from the object 155 at the same time. In an embodiment, when the image range of the photography device 130 is wide enough to cover the object 155, the object 155 should be accurately taken so that the object 155 is right in the center of the image range. Therefore, the controller 140 should make the photography device 130 wait and not start to follow and shoot the object 155 until a half (50%) of the object passes the lens center of the photography device 130. In some embodiments, when the image range of the photography device 130 can only cover half of the object 155, the controller 140 makes the photography device 130 respectively capture an image from the object 155 when 25% and 75% of the object 155 passes the lens center of the photography device 130. Those skilled in the art can capture images from objects having various sizes with this manner. Note that the duration that the photography device 130 follows and captures an image of the object 155 is at least longer than the shutter time of the photography device 130 which is required for capturing the image of the object 155.

In order to simplify the imaging procedure, it is preferred that the image range of the photography device 130 covers the entire object 155. In a preferred embodiment, the controller 140 of the present invention can further adjust the height of the photography device 130 according to the width of the object 155 so that the whole object can be in the range of the images captured by the photography device 130. In this manner, the focus of the photography device 130 can be locked, the error prone focusing process can be eliminated, and the quality of image capture can be further enhanced.

In addition, in some embodiments, the dynamic imaging system of the present invention further comprises a database (database 180 as shown in FIG. 1) and an inspection device (for example, integrated into the controller 140). The database 180 can be used to store the captured images of the object 155, and the inspection device can be used to inspect whether the object 155 conforms to a standard by comparing the captured images of the object 155 with a standard image.

Dynamic Imaging Method

Figure 2:
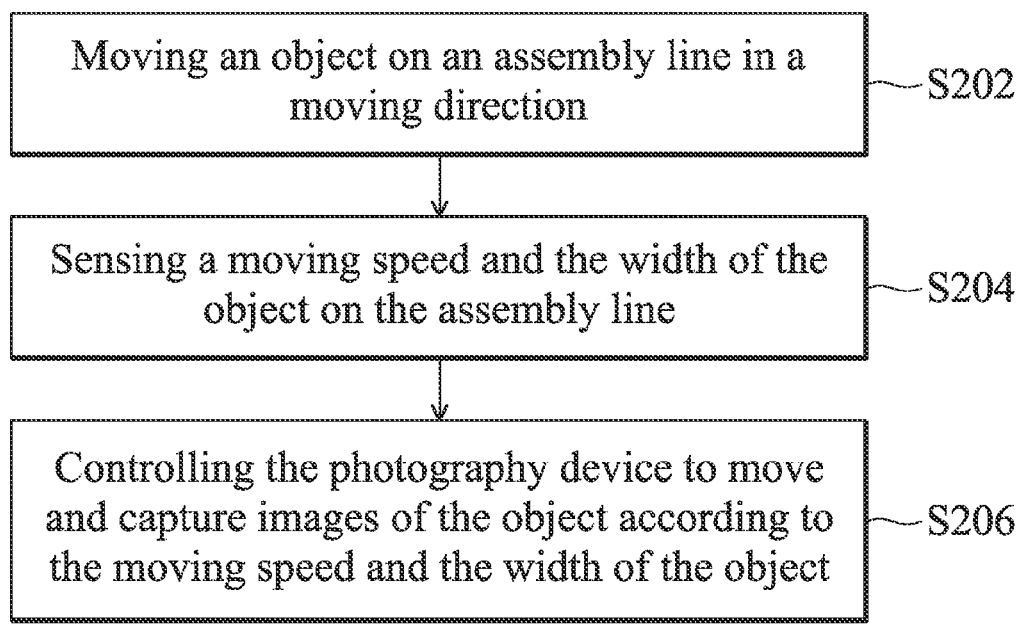
FIG. 2 is a flowchart of the dynamic imaging method according to an embodiment of the present invention.

In addition to the dynamic imaging system, the present invention further provides a dynamic imaging method. FIG. 2 is a flowchart of the dynamic imaging method according to an embodiment of the present invention. The dynamic imaging method comprises: in step S202, moving an object on an assembly line in a moving direction; in step S204, sensing a moving speed and the width of the object on the assembly line; and in step S206, controlling the photography device to move and capture images of the object according to the moving speed and the width of the object. Since the present method can be implemented with reference to the dynamic imaging system 100 as described above, its other embodiments will not be further discussed here.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A dynamic imaging system, comprising:
    an assembly line, for an object to be placed thereon and for moving the object in a moving direction;
    a sensor set, for sensing a moving speed and the width of the object on the assembly line;
    a photography device, for capturing images of the object; and
    a controller, coupled to the sensor set and the photography device, for controlling the photography device to move and capture images of the object according to the moving speed and the width of the object.

2. The dynamic imaging system as claimed in claim 1, wherein the controller further causes the photography device to follow and capture images of the object with the moving speed.

3. The dynamic imaging system as claimed in claim 2, wherein the controller further causes the photography device to wait and not start to follow and capture images of the object with the moving speed until a half of the object has passed a lens center of the photography device.

4. The dynamic imaging system as claimed in claim 2, wherein the duration that the photography device follows and captures an image of the object is at least longer than the shutter time of the photography device required for capturing the image of the object.

5. The dynamic imaging system as claimed in claim 1, wherein the controller further adjusts the height of the photography device according to the width of the object so that the whole object can be in the range of the images captured by the photography device.

6. The dynamic imaging system as claimed in claim 1, wherein the sensor set comprises:
    a first sensor, disposed on a first terminal of a measuring region of the assembly line, for recording a first leading-edge-triggered time when a leading edge of the object passes the first terminal of the measuring region; and
    a second sensor, disposed on a second terminal of the measuring region of the assembly line, for recording a second leading-edge-triggered time when the leading edge of the object passes the second terminal of the measuring region.

7. The dynamic imaging system as claimed in claim 6, wherein the controller calculates the moving speed based on the first leading-edge-triggered time, the second leading-edge-triggered time, and the length of the measuring region, wherein the length of the measuring region is the distance between the first terminal and the second terminal of the measuring region.

8. The dynamic imaging system as claimed in claim 1, wherein the sensor set comprises:
   a first sensor, disposed on a first terminal of a measuring region of the assembly line, for respectively recording a first leading-edge-triggered time and a first trailing-edge-triggered time when a leading edge and a trailing edge of the object passes the first terminal of the measuring region.

9. The dynamic imaging system as claimed in claim 8, wherein the controller calculates the width of the object according to the first leading-edge-triggered time, the first trailing-edge-triggered time and the moving speed of the object.

10. The dynamic imaging system as claimed in claim 1, wherein the sensor set comprises:
   a second sensor, disposed on a second terminal of a measuring region of the assembly line, for respectively recording a second leading-edge-triggered time and a second trailing-edge-triggered time when a leading edge and a trailing edge of the object passes the second terminal of the measuring region.

11. The dynamic imaging system as claimed in claim 10, wherein the controller calculates the width of the object according to the second leading-edge-triggered time, the second trailing-edge-triggered time and the moving speed of the object.

12. The dynamic imaging system as claimed in claim 1, further comprising an inspection device for inspecting whether the object conforms to a standard by comparing the captured images of the object with a standard image.

* * * * *